United States Patent
Corzani et al.

(10) Patent No.: US 10,953,129 B2
(45) Date of Patent: Mar. 23, 2021

(54) WETNESS INDICATOR COMPOSITIONS COMPRISING LEUCO DYES

(71) Applicant: Savarè I.C. S.r.l., Milan (IT)

(72) Inventors: Italo Corzani, Milan (IT); Thomas James Klofta, Cincinnati, OH (US); Laveeta Joseph, Cincinnati, OH (US); Johannson Jimmy Tee, Jr., Cincinnati, OH (US)

(73) Assignee: SAVARÈ I.C. S.R.L., Milan (IT)

( * ) Notice: Subject to any disclaimer, the term of this patent is extended or adjusted under 35 U.S.C. 154(b) by 244 days.

(21) Appl. No.: 15/565,832

(22) PCT Filed: Apr. 13, 2016

(86) PCT No.: PCT/IB2016/000468
§ 371 (c)(1),
(2) Date: Oct. 11, 2017

(87) PCT Pub. No.: WO2016/166592
PCT Pub. Date: Oct. 20, 2016

(65) Prior Publication Data
US 2018/0110896 A1     Apr. 26, 2018

Related U.S. Application Data

(60) Provisional application No. 62/147,258, filed on Apr. 14, 2015.

(30) Foreign Application Priority Data

Feb. 11, 2016 (IT) ........................ 102016000014334

(51) Int. Cl.

| | |
|---|---|
| *A61L 15/56* | (2006.01) |
| *C09D 11/037* | (2014.01) |
| *C09D 11/34* | (2014.01) |
| *C09D 11/10* | (2014.01) |
| *C09D 11/50* | (2014.01) |
| *C09B 67/28* | (2006.01) |
| *A61F 13/00* | (2006.01) |
| *B01J 20/28* | (2006.01) |
| *B65D 79/02* | (2006.01) |
| *C09D 11/106* | (2014.01) |

(52) U.S. Cl.
CPC ........ *A61L 15/56* (2013.01); *A61F 13/00063* (2013.01); *B01J 20/28033* (2013.01); *B65D 79/02* (2013.01); *C09B 67/0077* (2013.01); *C09D 11/037* (2013.01); *C09D 11/10* (2013.01); *C09D 11/106* (2013.01); *C09D 11/34* (2013.01); *C09D 11/50* (2013.01)

(58) Field of Classification Search
CPC ............... A61L 15/56; A61F 13/00063; C09B 67/0077; C09D 11/106; C09D 11/50; C09D 11/34; C09D 11/10; C09D 11/037; B65D 79/02; B01J 20/28033
See application file for complete search history.

(56) References Cited

U.S. PATENT DOCUMENTS

| | | | |
|---|---|---|---|
| 2009/0022434 A1* | 1/2009 | Chiba ................... | B32B 15/20 383/109 |
| 2009/0326494 A1 | 12/2009 | Uchida et al. | |
| 2013/0066289 A1* | 3/2013 | Song ....................... | A61L 15/56 604/361 |
| 2014/0087181 A1 | 3/2014 | Klofta et al. | |
| 2014/0088530 A1 | 3/2014 | Klofta et al. | |
| 2014/0088531 A1 | 3/2014 | Klofta et al. | |
| 2014/0088532 A1 | 3/2014 | Klofta et al. | |
| 2014/0088533 A1* | 3/2014 | Joseph ................... | A61L 15/56 604/361 |
| 2014/0275381 A1* | 9/2014 | Ribi ........................ | C09D 5/00 524/317 |
| 2014/0324004 A1* | 10/2014 | Song ....................... | A61L 15/56 604/359 |
| 2015/0005726 A1* | 1/2015 | Hippe .................... | A61F 13/514 604/361 |
| 2016/0303275 A1 | 10/2016 | Laveeta et al. | |

FOREIGN PATENT DOCUMENTS

| | | |
|---|---|---|
| EP | 2 067 458 A1 | 10/2009 |
| JP | 2607361 B2 * | 5/1997 |

* cited by examiner

*Primary Examiner* — Dennis White
(74) *Attorney, Agent, or Firm* — Pearne & Gordon LLP

(57) ABSTRACT

The present invention relates to wetness indicator compositions that comprise at least one leuco dye and one color developer in a hot-melt adhesive matrix. Upon contact with water or with water-containing fluids, said wetness indicator compositions are apt to change their color from a colorless state to a colorful state or from a first colored state to a second colored state having a color different from the first one; in particular, from a first colorless, white, or translucent state to a second state having a visible color, or vice versa. The disclosed wetness indicator compositions can be used as wetness/fluid indicators in various applications, e.g. in packaging articles and in absorbent articles; in an absorbent mat or sheet or operatory cloth for medical use; in a wound dressing product; in an absorbent mat or sheet for food products.

16 Claims, No Drawings

WETNESS INDICATOR COMPOSITIONS COMPRISING LEUCO DYES

This application is a National Stage application of PCT international application PCT/IB2016/000468, filed on Apr. 13, 2016 which claims the priority of Italian Patent Application No. 102016000014334, filed with the Italian Patent Office on Feb. 11, 2016, which claims priority of U.S. Provisional Application No. 62/147,258, filed with the U.S. Patent Office on Apr. 14, 2015, all of which are incorporated herein by reference in their entirety.

FIELD OF INVENTION

Disclosed in the present invention are wetness indicator compositions comprising hot-melt adhesives and leuco dyes. Upon contact with water or with water-containing fluids, said wetness indicator compositions change their color from one colorless state to a colorful state or from a first colored state to a second colored state, said second colored state having a color different from the first one.

Therefore the disclosed compositions can be used as wetness and/or aqueous fluid indicators in various applications, e.g. in hygienic absorbent articles, in absorbent articles for medical use, in absorbent articles for food packaging, in packaging articles and, generally speaking, in devices for detecting water in closed environments. The invention therefore also relates to said articles.

BACKGROUND OF THE INVENTION

In various fields of use and related articles, there is the need to signal to the user that a certain object or article, that is initially kept in a substantially dry state, has been in contact with liquid water or with water containing fluids or that it now contains water or aqueous fluids that were not initially present. Examples of similar applications may be certain foods that are preferentially packaged in a dry state and must be kept in such a state, certain chemicals or medical drugs that may be degraded by water or hygienic disposable absorbent articles that need to be changed when they are full of urine or of other aqueous body fluids.

All systems that can signal to a user the contact with water or the presence of liquid water or of water containing fluids, are here on the whole defined as "wetness indicators". For example the signal on which many wetness indicator systems work may be a change in color, from a first color that the wetness indicator shows in the initial, substantially dry state of the article on which it is applied, to a second different color in the wet state.

One of the two different colors between which the appearance of the wetness indicator changes upon contact with water or aqueous fluids can be a white or substantially colorless state. In certain fields of use and related articles, especially an initially (in the dry state) white or substantially colorless wetness indicator may also be a preferred choice, obviously provided that said indicators are then apt to change their appearance to a visible color once they get in contact with a water containing liquid; typical examples are food packaging or hygienic absorbent articles. In both these exemplary cases, an initial white or substantially colorless appearance of the wetness indicator composition is generally connected, in the perception of most users, to concepts like "hygiene" "cleanliness" or "well preserved", thus being much more liked by consumers.

Wetness indicator compositions may therefore comprise a colorant adapted to change in appearance, i.e., appear, disappear and in general change its initial color, etc., upon contact—together with the article to which the wetness indicator composition is associated—with liquid water or with fluids containing water as their main component. For example, in the case of hygienic absorbent articles, said fluids containing water as their main component are physiological body fluids such as urine, runny bowel movements, menses, etc. and the change of color appearance indicates here the need for the user to change the already exhausted disposable hygienic absorbent article. In other applications, e.g. in packaging water sensitive food or medical drugs, the change of color appearance may show that the product has not been preserved in the correct way and therefore the need of discarding the same.

However the active colorant mostly used as wetness indicator compositions for hygienic absorbent articles have an initial highly colorful state; in particular in most cases they are yellow in the initial dry state, i.e. before being contacted by water or physiological fluids, while change to a different color, e.g. blue or purple, when wetted.

Therefore, in above said applications, there is a continuing need for wetness/fluid indicators that can provide a variety of final wet color options, in presence of water, while starting preferably from a colorless/white initial dry state of the wetness indicator. There is also a continuing need for novel technical ways to incorporate such wetness indicators to the articles to which they are associated, that may offer improvements in manufacturing processes related to said application.

The object of the present invention is therefore to offer a wetness indicator composition according to a new concept, apt to simultaneously satisfy both the above mentioned market needs.

In particular, a first object of the invention is to provide a wetness indicator composition that, in the anhydrous state, is colorless or white and that in the wet state instead shows a strong and bright color.

A second object of the invention is then to provide a wetness indicator composition that may simplify and improve the application process of the composition into various articles with which it may be associated, in particular by providing said composition with: a good adhesion strength onto the widest variety of substrates used in the articles to which it must be associated, especially paper, cardboard and plastic of all possible kinds; a very high adhesion speed; an excellent storage stability over time without giving rise to undesired color changes; said composition being also preferably free from any flammable, volatile or toxic solvents.

SUMMARY OF THE INVENTION

The needs and objects highlighted above are achieved, according to the present invention, through a wetness indicator composition comprising a matrix formed by a hot-melt adhesive, at least one leuco dye and at least one color developer. Other preferred features of the wetness indicator composition of the present invention are defined in the secondary claims. The invention also comprises an article to a structural component of which said composition is incorporated; for example, said article could be a packaging; an absorbent mat or sheet or operatory cloth for medical use; a wound dressing product; an absorbent mat or sheet for food products.

However, from the scope of protection of the present invention the use of the invention composition in articles for baby care and feminine care is expressly excluded.

DETAILED DESCRIPTION OF THE PREFERRED EMBODIMENTS

According to the present invention, in order to positively address the needs outlined above, it is proposed to use as wetness indicator a leuco (i.e. colorless) dye or a blend of leuco dyes that changes to a visible color upon contact with water or by water-containing physiological fluids, said dyes being dispersed into a hot-melt adhesive matrix and with the further addition of a color developer.

Prior art teaches to incorporate wetness indicators comprising leuco dyes into various types of liquid carriers/vehicles/binding matrixes etc., such as inks (solvent based or water based), liquid adhesives (solvent based or water based), varnishes, and the like. On the contrary, the incorporation of leuco dye or a blend of leuco dyes as wetness indicator(s) into a hot-melt adhesive solid matrix has never been disclosed in the prior art.

Notwithstanding said incorporation must be carried out through a careful selection of the chemical nature of all the components of the hot-melt adhesive matrix, so as not to impair the leuco dyes features, such hot-melt matrix offers several advantages that are typical of hot-melt adhesives: e.g. easy and fast application from the molten state, strong adhesion on most possible substrates, even on those difficult to bond as plastic films, like the polyolefin plastic films that are used in hygienic absorbent articles or various types of packaging, absence of toxic, volatile or flammable solvents, very high gluing rate, absence of water (that of course may prematurely trigger the development of colors or adversely affect the product onto which the composition is applied) in all phases of the wetness indicator composition processing and application and other positive features typical of the hot-melt adhesives.

Definitions

"Baby care or feminine care articles" refers to products and/or methods related to disposable absorbent and/or non-absorbent articles including adult incontinence garments, bibs, diapers, training pants, infant and toddler care wipes; catamenial pads, incontinence pads, interlabial pads, panty liners, pessaries, sanitary napkins, tampons and tampon applicators, and/or wipes.

As used herein, the term "colorant" refers to any dye, ink, inks that comprise dyes or pigments, pH indicators, chemical indicators and metal chelants, oxidation or reduction (redox) indicators, ionochromic colorants, halochromic colorants, solvatochromic colorants, hydrochromic colorants, thermochromic colorants, electrochromic colorants, biochromic colorants that change color upon contact with a specific biological component of an exudate, and any material that has the ability of changing its color or the color of its environment in certain specific conditions, and any combination thereof.

As used herein, the term "permanent colorant" refers to a colorant that maintains its color independent of environmental factors or one that does not change its color under any circumstance, such as a pH change or exposure to a liquid or specific components of the liquid, or due to high humidity, or high or low temperatures.

"Comprise," "comprising," and "comprises" are open ended terms, each specifies the presence of what follows, but does not preclude the presence of other features, e.g., elements, steps, components known in the art, or disclosed herein.

Leuco Dyes

The wetness indicator compositions that are utilized in the present invention comprise at least one leuco dye and at least one color developer formulated into a hot-melt adhesive matrix. In this way the wetness indicator composition changes in appearance, i.e. changes color, appears, disappears, etc., upon contact, within the article in which the wetness indicator composition is contained, upon contact with liquid water or with fluids mainly containing water like physiological body fluids. In a particular embodiment of the present invention the formulated wetness indicator compositions of the present invention, upon contact with liquid water or with fluids mainly formed by water like physiological body fluids, change their color from an initial white or substantially colorless state, in the dry state, to a colorful state or vice versa, after being wetted with the liquid aqueous phase.

A leuco dye (from the Greek word LEUKOS=WHITE) is a dye whose molecule can acquire two chemical forms, one of which is substantially colorless. As already briefly said above for all dyes, also leuco dyes are often classified according to the different chemical mechanisms that cause the change of the dye molecule from its substantially colorless (LEUCO) form to a colorful form. Therefore in literature it is possible to find leuco dyes classified in families like for example thermochromic leuco dyes, in which the color change from a colorless to a colorful state (or vice versa) is caused by a temperature variation; photochromic leuco dyes in which the change from a colorless to a colorful state (or vice versa) is caused by light; solvatochromic leuco dyes in which the change from a colorless to a colorful state (or vice versa) is caused by the contact with specific solvents and especially with a solvent of a certain well defined polarity; biochromic leuco dyes in which the change from a colorless to a colorful state (or vice versa) is caused by the contact with specific biological entities or components; redox leuco dyes in which the change from a colorless to a colorful state (or vice versa) is caused by chemical oxidation or reduction; electrochromic leuco dyes whose change from a colorless to a colorful state (or vice versa) is caused by the passage of an electric current; ionochromic leuco dyes in which the change from a colorless to a colorful state (or vice versa) is caused by the interaction with specific ions and/or by a variation in their concentration; halochromic leuco dyes in which the change from a colorless to a colorful state (or vice versa), according to the original literal meaning of the word (from the Greek word HALOS=SALT), is caused by the interaction with specific salts etc.

It is however necessary to notice that in current common technical-scientific jargon today the word "halochromic" is often used for dyes and leuco dyes that change from an initial color (which is a colorless state, for leuco dyes) to a different colorful state due to a variation in the concentration of hydrogen ions. In this slightly different meaning, therefore, halochromic leuco dyes form a subset of the more general ionochromic leuco dyes, when the ions whose variation in concentration causes the change of the leuco dye from a colorless to a colorful state or vice versa, are hydrogen ions.

Without being bound by theory, a color developer is any substance that by interacting or reacting with the leuco dye makes it change its color from a colorless to a colorful state or vice versa, independently from the chemical nature of the developer(s) and independently from the nature of the chemical or physical mechanism that activates and causes the color change.

Because the compositions disclosed in the present invention are intended to be used as wetness indicators, in contact with liquid water or with aqueous fluids, it is obvious, just for clarity and without limitations of the scope of the present invention, that the general scheme of how the compositions of the present invention possibly work, is as follows: the contact between the disclosed compositions and liquid water or aqueous fluids, like biological fluids, is the "triggering event" that starts the interaction or reaction between the present leuco dye(s) and the present developer(s) that cause the change of appearance from a colorless to a colorful state (or vice versa), independently from the nature of the chemical or physical mechanism of said interaction or reaction and independently from the chemical nature of the developer(s).

In a particular embodiment of the present invention the color developer may function as a Bronsted or Lewis acid or a strong hydrogen bonding ingredient, causing the colorless leuco dye to change to a colorful dye.

For example, one particular leuco dye is crystal violet lactone, a phthalide based colorant (spirolactone) hereinafter abbreviated as CVL and chemically named as 3,3-Bis (p-dimethylaminophenyl)-6-dimethylaminophthalide or 6-(Dimethylamino)-3,3-bis [p-(dimethylamino) phenyl] phthalide, also identified by the CAS Number 1552-42-7.

CVL is colorless when its five membered lactone ring structure remains intact. When reacted with a suitable developer like certain Lewis acid electron acceptor molecules, the lactone ring typically breaks open, resulting in a highly conjugated CVL molecule with multiple resonance structures. This highly conjugated ring-opened CVL molecule now appears blue to the naked eye. The CVL ring-opening reaction occurs due to dissociation of the C—O bond in the presence of a proton donor or electron pair acceptor or even strong hydrogen bonding agents. This ring-opening reaction results in the formation of the highly conjugated and ring-opened blue cation. This colorless to blue colored reaction makes CVL an attractive active colorant not only for use within wetness indicator compositions, but also as a photo-polymerization initiator and as the main active colorant in many thermochromic materials.

As noted, the CVL lactone ring opening results from the reaction with a suitable molecule, which could act as a color developer. Many developers have the ability to donate a proton(s) to the CVL or accept electrons from the CVL molecule. This acidity of the developer leads to the ring opening of the CVL that, in turn, causes the color change from colorless to blue. Not to be bound by theory, but the colorless ring-closed form of CVL is also referred to as its spiropyran form where the spiro carbon is sp3 hybridized and the 5-membered lactone ring remains closed and intact. This sp3 hybridization of the spiro carbon limits the conjugation of the CVL such that the ring-closed form of CVL remains substantially colorless to the naked eye. But, upon exposure to a proton(s) donating molecule, like a Bronsted acid, or an electron accepting molecule, like a Lewis acid, the lactone ring of CVL-opens as result of bond breakage of the oxygen to the spiro carbon. With the ring opening, the spiro carbon now becomes sp2 hybridized and multiple resonance structures are possible in this highly conjugated molecule. With this enhanced resonance and conjugation of bonds in the ring-opened CVL structure, the CVL molecule becomes intensely blue in color. It should be noted that mixtures of Bronsted acids and Lewis acids could be used in the same formula, in view to enhance the composition properties.

Not only does proton donation lead to the CVL's ring opening, but molecules with strong hydrogen bonding capabilities and/or Lewis acid properties can also induce the CVL's lactone ring-opening reaction. In addition to these compounds, certain cationic atoms like mercury and copper, are known to intensify the blue color by complexing with the open ring CVL structure.

For a generic developer that is a proton donor, the reaction is depicted as in the following drawing, wherein the five membered lactone ring structure on the left is colorless and the protonated structure on the right is blue:

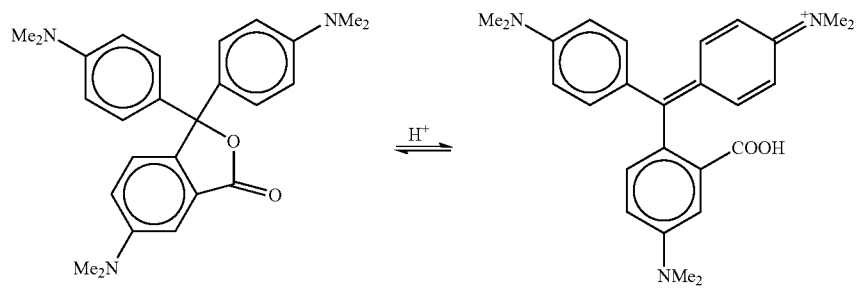

Also other phthalide dyes, especially the ones having the same basic molecular structure of CVL may change from a colorless to a strongly colored state through a similar chemical mechanism and can be equally used in the present invention. Preferred leuco dyes of such type are for example heterocyclic analogues of CVL, in particular the ones with indole and pyridine rings, an example of which is 3-(1,2-Dimethyl-3-indolyl)-3-[4-(diethylamino)-2-methylphenyl] phthalide, identified also with the CAS number 36499-49-7 and also commercially known with the trade dye name of NC BLUE 3.

Other types of leuco dyes, in changing to a colorful state, function by different chemical mechanisms. For example, the colorless to colored change and vice versa in the leuco-quinone class of leuco dyes is activated by redox reactions. Other classes of leuco dyes are light activated and these include leuco derivatives of the oxazine, thiazine, and phenazine dyes. Other leuco dyes may change from a colorless to a colored state when activated by the presence and concentration of certain specific ions and therefore by the presence of some chemical compounds (like acids, salts etc.) capable of releasing certain active ions. Such leuco dyes are known as ionochromic or halochromic. In a particular embodiment of the present invention these active ions are hydrogen ions, and said ionochromic/halochromic leuco dyes can therefore be used also as pH indicators. Examples of ionochromic leuco dyes of this type usable in the present invention, include e.g. thymolphthalein, alpha-naphtholphthalein, 4,5,6,7-tetrabromo-phenolphthalein, 3',3'',5',5''-tetrabromo-phenolphthalein, o-cresolphthalein, phenolphthalein, xylenolphthalein, guiacolphthalein, ethyl bis (2,4-dinitrophenyl) acetate, bis-[9-(diethylamino)-5H-benzo[a]phenoxazin-5-iminium] sulfate (Nile Blue A), Quinoline Blue, Heptamethoxy Red, 3-nitrophenol, pinachrome.

Additional specific leuco dyes besides crystal violet lactone and the previously mentioned ones that can be usefully employed in the present invention, may include, for example, other phthalide leuco dyes, triarylmethane leuco dyes, thiazine, oxazine and phenazine leuco dyes; leuco quinones; fluoran leuco dyes etc. Examples of such colorant may include:

(1) triarylmethane-based leuco dyes, e.g. 3,3-bis(p-dimethylaminophenyl)phthalide, 3-(p-dimethylaminophenyl)-3-(1,2-dimethylindol-3-yl) phthalide, 3-(pdimethylaminophenyl)-3-(2-methyl-indol-3-yl) phthalide, 3,3-bis(1,2-dimethylindol-3-yl)-5-dimethyl-aminophthalide, 3,3-bis(1,2-dimethylindol-3-yl)-6-dimethyl-amino-phthalide, 3,3-bis(9-ethylcarbazol-3-yl)-6-dimethylaminophtha-lide, 3,3-bis(2-phenylindol-3-yl)-6-dimethylamino phthalide, 3-pdimethyl-aminophenyl-3-(1-methylpyrrol-3-yl)-6-dimethylaminophtha-lide, etc.

(2) diphenylmethane-based dyes, e.g., 4,4'-bisdimethylaminobenzhydryl benzyl ether, N-halophenylleucoauramine, N-2,4,5-trichlorophenyl-leucoauramine, etc.

(3) lactam-based dyes, e.g., rhodamine-B-anilinolactam, rhodamine-(p-nitroanilino)lactam,rhodamine-(o-nitroanilino)lactam, etc.

(4) fluoran-based dyes, e.g., 3-dimethylamino-7-methoxy fluoran, 3-diethylamino-6-methoxyfluoran, 3-di-ethyl-amino-7-methoxy fluoran, 3-diethylamino-7-chloro fluoran, 3-diethylamino-6-methyl-7-chloro fluoran, 3-di-ethyl-amino-6,7-dimethyl fluoran, 3-(N-ethyl-p-toluidino)-7-methyl fluoran, 3-diethylamino-7-(N-acetyl-N-methyl-amino) fluoran, 3-diethylamino-7(N-methylamino) fluoran, 3-diethylamino-7-dibenzylamino fluoran, 3-diethylamino-7-(N-methyl-N-benzylamino) fluoran, 3-diethylamino-7-(N-chloroethyl-N-methylamino) fluoran, 3-diethylamino-7-N-diethylamino fluoran, 3-(N-ethyl-p-toluidino)-6-methyl-7-phenylamino fluoran, 3-(N-ethyl-p-toluidino)-6-methyl-7-(p-toluidino) fluoran, 3-diethylamino-6-methyl-7-phenylamino fluoran, 3-dibutylamino-6-methyl-7-phenylamino fluoran, 3-diethylamino-7-(2 carbomethoxy-phenyl-amino) fluoran, 3-(N-cyclohexyl-N-methylamino)-6-methyl-7-phenylamino fluoran, 3-pyrrolidino-6-methyl-7-phenylamino fluoran, 3-piperidino-6-methyl-7-phenylamino fluoran, 3-diethylamino-6-methyl-7-(2,4-dimethylamino) fluoran, 3-diethylamino-7-(o-chlorophenylamino) fluoran, 3-dibutylamino-7-(o-chlorophenylamino) fluoran, 3-pyrrolidino-6-methyl-7-(p-butylphenylamino) fluoran, 3-(N-methyl-N-n-amylamino)-6-methyl-7-phenylaminofluoran, 3-(N-ethyl-N-n-amylamino)-6-methyl-7-phenylamino fluoran, 3-(N-ethyl-N isoamylamino)-6-methyl-7-phenylamino fluoran, 3-(N-methyl-N-n-hexylamino)-6-methyl-7-phenylamino fluoran, 3-(N-ethyl-N-n-hexylamino)-6-methyl-7-phenylamino fluoran, 3-(N-ethyl-N-[3-ethylhexylamino)-6-methyl-7-phenylamino fluoran, etc.

Further examples of leuco dyes useful in the present invention may include Malachite Green Lactone, Leuco Indigo, Leuco Methylene Blue, Benzoyl Leuco Methylene Blue etc. The dyes useful in this invention are not limited to those exemplified above, and one or two or more in admixture, may be used in the present invention.

The wetness indicator compositions of the present invention may comprise from about 0.01% to about 20% by weight of a leuco dye or of a blend of leuco dyes. The wetness indicator compositions may also comprise other colored non-leuco compounds. These other colored compounds may be a permanent colorant, an ink, a pigment like e.g. titanium dioxide or aluminum silicates, or zinc oxide, a pH indicator, a redox indicator, and combinations thereof. In such last instances, the total amount of leuco dyes plus other colored compounds in the wetness indicator composition may range from about 0.02% to about 30% by weight. In some cases, it may be advantageous to include an oil-soluble or water-soluble permanent colorant, Some examples of oil soluble permanent colorants include D&C Yellow No. 11, D&C Red No. 17, D&C Red No. 21. D&C Red No. 27, D&C Violet No. 2, D&C Green No. 6, and D&C Orange No. 5. Additional permanent colorants include Pigment Red 146 (CAS #5280-68-2), Pigment Red 122 (CAS #980-26-7), Pigment Orange 16 (CAS #6505-28-8), red beet extract, and beta-carotene.

Some representative examples of liquid-activated colorants that can be used in the practice of this invention include: Malachite green, brilliant green, crystal violet, erythrosine B, methyl green, methyl violet 2D, picric acid, naphthol yellow S, quinaldine red, eosine Y, metanil yellow, m-cresol purple, thymol blue, xylenol blue, basis fuchsin, eosin B, 4-p-aminophenol(azo)benzenesulphonic acid-sodium salt, cresol red, m-cresol red, m-cresol purple, martius yellow, phloxine B, acid phloxine, methyl yellow, bromophenol blue, congo red, methyl orange, crystal violet lactone, ethyl bis(2,4-dinitrophenyl) acetate, bromochlorophenol blue (water soluble or free acid form), ethyl orange, flourocene WS, bromocresol green, chrysoidine, methyl red sodium salt, alizarine red S—$H_2O$, cochineal, chlorophenol red, bromocresol purple, 4-naphtha, alizarin, nitrazine yellow, bromothymol blue, brilliant yellow, neutral red, rosalic acid, phenol red, 3-nitro phenol, orange II, phenolphthalein, o-cresolphthalein, nile blue A, thymolphthalein, aniline blue WS, alizarine yellow GG, mordant orange, tropaolin O, orange G, acid fuchsin, thiazol yellow G, indigo carmine, cresol red, methyl red, p-nitrophenol, and alizarin yellow R. In certain instances, it is advantageous to use the free acid form, free base form, or salt form of the colorants, or mixtures thereof.

Additional water-soluble colorants may include FD&C Blue No. 1, FD&C Blue No. 2, FD&C Green No. 3, FD&C Red No. 40, FD&C Red No. 4, FD&C Yellow No. 5, FD&C Yellow No. 6, C.I. Food Blue 5, and C.I. Food Red 7, D&C Yellow No. 10, D&C Yellow No. 7, D&C Yellow No. 2, D&C Yellow No. 8, D&C Orange No. 4, D&C Red No. 22, D&C Red No. 28, D&C Red No. 33, D&C Green No. 8, D&C Green No. 5, D&C Brown No. 1, and any combination thereof. Preferably, the colorant is soluble within the wetness indicator composition, but, as noted in certain instances, the colorant can function as intended by homogeneously suspending or dispersing it within the wetness indicator composition.

Additional suitable fluid colorants include water soluble colorants like direct dyes, acid dyes, base dyes, and various solvent-soluble colorants. Dispersed or suspended pigment colorants can also be employed into these wetness indicator compositions (liquid-activated formulations). Examples include, but are not limited to, C.I. Acid Yellow 73, C.I. Solvent Yellow 94, C.I. Acid Yellow 74, C.I. Solvent Orange 32, C.I. Solvent Red 42, C.I. Acid Orange 11, C.I. Solvent Red 72, C.I. Pigment Orange 39, C.I. Solvent Orange 18, C.I. Acid Red 87, C.I. Solvent Red 43, C.I. Pigment Red 90:1, C.I. Solvent Red 44, C.I. Solvent Red 45, C.I. Solvent Orange 16, C.I. Acid Red 91, C.I. Acid Red 98, C.I. Acid Red 92, C.I. Solvent Red 48, C.I. Pigment Red 174, Pigment Red 146 (C.I. No. 12485, CAS #5280-68-2)), Pigment Red 122 (CAS #980-26-7), Pigment Red 112 (CAS #6535-46-2), Pigment Red 101 (CAS #1309-37-1), Pigment Orange 34 (CAS #15793-73-4, Pigment Orange 16 (CAS #6505-28-8), Pigment Green (CAS #1328-53-6), Pigment Blue 15:2 (CAS #12239-87-1), Pigment Blue 15 (CAS #147-14-8), Pigment Black 7 (CAS #1333-86-4), Pigment Red 176, Pigment Red 200, Pigment Red 254, Pigment Red 48:1, Pigment Red 48:2, Pigment Red 48:3, Pigment Red 52, Pigment Red 52:1, Pigment Red 57:1, Pigment Red 63:1, Pigment Violet 19, Pigment Violet 23, Pigment Yellow 12, Pigment Yellow 13, Pigment Yellow 14, Pigment Yellow 17, Pigment Yellow 74, Pigment Yellow 83, C.I. Acid Red 95, C.I. Solvent Red 73, C.I. Pigment Red 191, C.I. Acid Red 51, C.I. Food Red 14, C.I. Pigment Red 172, C.I. Solvent Red 140, C.I. Acid Red 93, C.I. Solvent Red 47, C.I. Acid Red 94, C.I. Solvent Red 141, C.I. Mordant Violet 25, C.I. Solvent Orange 17, C.I. Solvent Red 46, D&C Red 27(C.I. 45410:1), D&C Orange 5(C.I. 45370:2), and combinations thereof. More preferred fluid colorants are selected from the group consisting of D&C Red 27, D&C Orange 5, and combinations thereof.

Additional suitable colorants may include bromopyrogallol red, bromoxylenol blue, methylene blue, monoazo dyes such as acid alizarin voliet N, monoazo pyrazoline dyes (such as acid yellow 34), diazo dyes (such as acid black 24), anthraquinone dyes (such as acid black 48), amphoteric anthraquinone dyes (such as acid blue 45),triphenylmethane dyes (such as acid fuchsin), phthalein type dyes (such as o-cresolphthalein), xanthene dyes (such as 2'7' dichlorofluorescein eosin B), heterocyclic acridine aromatics(such as acridine orange), diphenylmethane dyes (such as auramine O), triphenylmethane dyes(such as basic fuchsin), cationic thiazine dyes(azure C), cationic anthraquinone dyes such as basic blue 47, phthalocyanine type dyes (such as strazon orange G), anthraquinone type (sch as alizarin), neutral complex dyes (such as azure A eosinate), terpene type dyes (such as trans-beta-carotene), as well as combinations including at least one of the foregoing dyes.

Examples of colorants further include, but are not limited to, organic dyes, inorganic pigments, colored macromolecules, colored nanoparticles and materials. Examples of dyes include acridine dyes, anthraquinone dyes, arylmethane dyes, azo dyes, nitro dyes, nitroso dyes, phthalocyanine dyes, quinone-imine dyes, Aazin dyes, Indophenol dyes, oxazin dyes, Oxazone dyes, Thiazole dyes, xanthene dyes, Fluorene dyes, fluorone dyes, rhodamine dyes and natural dyes like beta-carotene, annatto, cochineal, caramel color, red beet extract, beet pigments, riboflavin, anthocyanin, carotenoids, apocarotenal, and paprika. Also suitable are caramelizing ingredients used to darken the color. Examples of pigments include Cadmium pigments: cadmium yellow, cadmium red, cadmium green, cadmium orange; Carbon pigments: carbon black (including vine black, lamp black), ivory black (bone char); Chromium pigments: chrome yellow and chrome green; Cobalt pigments: cobalt violet, cobalt blue, cerulean blue, aureolin (cobalt yellow); Copper pigments: Azurite, Han purple, Han blue, Egyptian blue, Malachite, Paris green, Phthalocyanine Blue BN, Phthalocyanine Green G, verdigris, viridian; Iron oxide pigments: sanguine, caput mortuum, oxide red, red ochre, Venetian red, Prussian blue; Clay earth pigments (iron oxides): yellow ochre, raw sienna, burnt sienna, raw umber, burnt umber; Lead pigments: lead white, cremnitz white, Naples yellow, red lead; Mercury pigments: vermilion; Titanium pigments: titanium yellow, titanium beige, titanium white like titanium dioxide, titanium black; Ultramarine pigments: ultramarine, ultramarine green shade; Zinc pigments: zinc white like zinc oxide, zinc ferrite. Other examples include alizarin, alizarin crimson, gamboge, cochineal red, rose madder, indigo, Indian yellow, Tyrian purple, organic quinacridone, magenta, phthalocyanine green, phthalocyanine blue, pigment red 170.

Color Developers

The wetness indicator compositions of the present invention comprise at least one color developer, said color developer being defined as any substance that by reacting with the leuco dye makes it change its color from a colorless to a colorful state.

When the chemical mechanism that activates the color change in the leuco dye is the opening of a lactone ring, like in CVL and of other molecules having an analoguos structure, color developers that can react with leuco dyes similar to CVL to break open the lactone ring include, for example, phenols, aromatic amines, other colorants, strong hydrogen bonding agents, Bronsted acids like carboxylic acids, Lewis acids, metal salts and mixtures thereof. Specific developers include for example phenolic compounds having one or more phenolic hydroxyls, like e.g. gallic acid and its esters like propyl gallate, octyl gallate, dodecyl (lauryl) gallate, butyl gallate, hexyl gallate, decyl gallate, mono-hydroxybenzoic acids and their salts and esters, and in particular 4-hydroxy-benzoic acid or salicylic acid and their salts and esters, like zinc salicylate, zinc salt of 3,5-bis(alpha-methylbenzyl) salicylic acid, sulfosalicylic acid and its salts and esters, 3,5-di-tert-butylsalicylic acid and its salts and esters, benzenediols and di-hydroxy-benzoic acids and their salts and esters, benzenetriols and other tri-hydroxy-benzoic acids and their salts and esters, besides the already cited gallic acid and its derivatives etc.

Other examples of color developers both with phenolic and non phenolic chemical nature that can be successfully used in the present invention are Benzyl 4-hydroxybenzoate, 4.4'-Dihydroxybenzophenone, 2,4'-dihydrohybenzophenone, 2,2',4,4'-Tetrahydroxybenzophenone, 2,2-bis(phydroxyphenyl) propane (common name of Bisphenol A), Bis(4-hydroxyphenyl)methane (common name of Bisphenol F), 4-Hydroxyphenyl sulfone (common name of Bisphenol S), bis-(3-allyl-4-hydroxyphenyl) sulfone, 4-[4'-[(1'-methylethyloxy) phenyl] sulfonyl]phenol, 4-hydroxyphenyl 4-isoprooxyphenylsulfone, Phenol, 4-[[4-(2-propen-1-yloxy)phenyl]sulfonyl], 4-Hydroxy-4'-benzyloxydiphenyl-sulfone, the Urea Urethane Compound with a CAS number of 321860-75-7, 4,4'-bis(N-carbamoyl-4-methylbenzenesulfonamide)diphenylmethane, 2,4'-Bis(hydroxyphenyl)sulfone, 4,4'-(1-Phenylethylidene)bisphenol (also known as Bisphenol AP), 2,2'-Bis(4-hydroxy-3-methylphenyl)propane (also known as Bisphenol C), Methyl bis(4-hydroxyphenyl) acetate, 4,4'-Isopropyllidenebis(2-phenylphenol), 1,7-bis(4-hydroxyphenylthio)-3,5-dioxaheptane, Bisphenol B, p-Methylphenol, m-Nitrobenzoic acid, m-Aminobenzoic acid, tannic acid, phenolpropenoic acid, 1,2,3-triazoles, thioureas, PERGAFAST 201 (Benzenesulfonamide, 4-methyl-N-[[[3[[(4-methylphenyl)sulfonyl]oxy]phenyl]amino] carbonyl]), D-90 Developer (identified also with CAS number 191680-83-8), acetylsalicylic acid (Aspirin) and its esters and salts, 2-carboxy-phenyl-salicylate (Salsalate), 2,3,4 trihydroxy-benzophenone, 4-hydroxy-benzophenone, 2,4 dihydroxy-acetophenone, benzyl-2,4-di-hydroxy-phenyl-ketone, thymol, monocyclic and polycyclic aromatic carboxylic acids, like phthalic acids or 1-naphthaleneacetic acid, other phenolic and polyphenolic acids, such as e.g. 4-hydroxybenzoic acid, vanillic acid, caffeic acid, gentisic acid, ferulic acid, ellagic acid etc. and their esters and salts.

Other examples of useful phenolic compounds are 4-tert-butylphenol, 4-acetylphenol, 4-tert-octylphenol, 4,4'-sec-butylidenephenol, 4-phenylphenol, 4,4'-dihydroxydiphenylmethane, 4,4'-isopropylidene diphenol, hydroquinone, 4,4'cyclohexylidene diphenol, 4,4-dihydroxy diphenylsulfide, 4,4'-thiobis(6-tert-butyl-3-methylphenol), 4,4'-dihydroxydiphenyl sulfone, hydroquinone monobenzyl ether, 2,4,4'tri-hydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, tolyl 4-hydroxybenzoate, chlorophenyl4-hydroxybenzoate, phenylpropyl 4-hydroxybenzoate, phenethyl 4-hydroxybenzoate, p-chlorobenzyl 4-hydroxybenzoate, p-methoxybenzyl 4-hydroxybenzoate, 1-naphthol, 2-naphthol, phenolic rosins, phenolic polymers and resins, and like phenol compounds.

Further examples of suitable developers include also inorganic compounds like Silica and natural or synthetic silicates like clays, zeolites and the like, as well inorganic and organic compounds of polyvalent metals like oxides, halides, carbonates, sulfates, nitrates, acetates, formates, oxalates, benzoates, acetylacetonates, stearates, salicylates, etc. of magnesium, aluminum, calcium, titanium, zinc, cadmium, nickel, cobalt, iron, manganese, vanadium etc. like magnesium chloride, calcium chloride, zinc chloride, zinc bromide, zinc iodide, zinc oxide, zinc stearate, zinc glicynate, zinc resinates, aluminum trichloride, aluminum oxide, aluminum stearate, aluminum glycinate, aluminum acetylacetonate etc. Silica and silicates as well as compounds of Zinc, Aluminum, Magnesium and Zinc are preferred; and, among metallic compounds, Zinc compounds are the most preferred. It has been in fact surprisingly found that especially Zinc compounds, like e.g. Zinc Oxide or Zinc salicylates (i.e the zinc salts of salicylic acid or the zinc salts of acids derived from salicylic acid), when used alone or together with another non-zinc containing developer, significantly strengthen the color to which leuco dyes turn upon contact with water and by reaction with the color developer(s).

It has also been surprisingly found that, especially when the used leuco dye is Crystal Violet Lactone (CVL) or one of its structurally similar analogues, it is preferable that the color developer or developers used in the present invention have a not too high solubility in water, for example equal or lower than 10 grams per liter at 20° C. and more preferably equal or lower than 5 grams per liter at 20° C. This helps in avoiding possible premature changes of color before actual contact with a substantial amount of liquid water, e.g. for possible absorption of humidity from moist air.

In a particular embodiment of the present invention, in the case that one or more ionohromic/halochromic leuco dyes are used, the color developer(s) may be also any chemical compound or blend of different chemical compounds, which are apt to release, upon addition of water or of water containing physiological fluids, the active ions that activate the leuco dye for changing from an initial colorless state to a final colorful state.

In a more particular embodiment, when such active ions are hydrogen ions, any chemical compound having in contact with water a distinct basic or acidic reaction (depending on the fact that the used leuco dye changes from its colorless to its colorful state in a basic or in an acidic environment), may work as developers. Examples of suitable developers for hydrogen ions activated ionochromic leuco dyes that are activated for color change in an acidic environment, are typical inorganic or organic acids like e.g., as non-limiting examples, phosphoric acid, citric acid, tartaric acid, sulfamic acid, benzensulfonic acid, stearic acid, isostearic acid, abietic acid, acidic rosins etc; as well as salts that in water have an acidic behavior like aluminum sulfate and its double sulfates (alums), hydrogen sulfates of Sodium and Potassium, Ammonium halides etc.

For ionochromic leuco dyes that are activated in a basic environment suitable developers may be for example inorganic or organic compounds and salts that in water have a distinct basic behavior, like e.g. hydroxides, carbonates and hydrogen carbonates of alkali and earth-alkali metals, stearates and oleates of Sodium and Potassium, Sodium tetraborate, tri-Sodium phosphate, guanidine carbonate, amines etc.

The wetness indicator compositions of the present invention comprise from about 0.1% to about 50.0% by weight of a color developer or of a blend of color developers, preferably from about 1.0% to about 30.0%.

Hotmelt Adhesive Matrix

The wetness indicator compositions that are utilized in this invention comprise a matrix that is a hot-melt adhesive. Preparing a hot-melt adhesive involves melting the components thereof together at an high temperature, typically from at least about 50° C. to about 180° C., in some embodiments preferably from about 60° C. to about 150° C., and more preferably from about 80° C. to about 130° C. In order to render the hot-melt adhesive matrix processable, the wetness indicator composition must be heated to a temperature high enough so as to insure that the adhesive flows readily but not so hot so as to cause degradation at an unacceptable rate. Thus, it is common to add antioxidants and other stabilizers, e.g. UV stabilizers, to the wetness indicator compositions of the invention in order to slow down the decomposition rate of the hot-melt adhesive matrix. The ingredients of the present invention's wetness indicator compositions are melted and blended together at high temperatures, typically in the above mentioned ranges of temperature, and then said compositions in liquid state are applied and adhered to a substrate while maintaining them at a sufficiently high temperature to keep the composition in liquid molten state.

The hot-melt adhesive matrix may comprise various components like typically a thermoplastic polymer or a blend of thermoplastic polymers, modifiers of the melt viscosity such as plasticizers and/or waxes, tackifiers for increasing the adhesion on a large variety of substrates, surfactants and wetting agents for improving the wetting and contact with water containing fluids, organic and inorganic fillers, antioxidants, stabilizers, colored compounds such as pigments and permanent dyes, perfumes etc.

Polymers, copolymers, terpolymers, and other macromolecular materials that can be used in the present invention as a hot-melt adhesive matrix material include for example ethylene vinyl acetates (EVA), styrenic block copolymers like SIS, SBS, SEBS, SIBS and the like, polyolefins like low density polyethylene (LDPE) and high density polyethylene (HDPE), atactic polypropylene and polypropylene homopolymers and copolymers, oxidized polyethylene, polybutene and poly-iso-butylene. Other possible polymers suitable for a hot-melt adhesive matrix according to the present invention are for example polymethyl methacrylate, ethylene methyl acrylate, ethylene ethyl acrylate, ethylene butyl acrylate, poly-vinyl pyrrolidone and its copolymers like poly-vinyl pyrrolidone-vinyl acetate copolymers, sulfopolyesters like the ones marketed by Eastman under the trademark AQ, poly-vinyl ethers, polyurethanes, polyamides, polyester block copolymers, polyether-ester block copolymers, polyether-amide block copolymers, polyether-ester amide block copolymers, polymethacrylic acid, polyacrylic acid and its salts even in the crosslinked form (which are not thermoplastic but may function as fillers), ethylene-acrylic acid copolymers, ethylene-methacrylic acid copolymers, the fully and partially neutralized salts of ionomers like the mentioned ethylene-acrylic acid copolymers, polyvinyl butyral, polyethylene oxide, polyvinyl alcohol, ethylene-vinyl alcohol copolymers, polycaprolactone, polylactic lactic acid and its copolymers e.g. with glycolic acid, polyglycolic acid, oxidized ethylene-vinyl acetate copolymers, ethylene maleic anhydride copolymers, propylene maleic anhydride copolymers, styrene maleic anhydride copolymers, polyethylene imines, polyacryl amides, polyacrylates.

Other polymers that can be used to the above purpose are also natural polymeric substances or derivates thereof as e.g. cellulose ethers and esters like methyl-cellulose, hydroxy-propyl cellulose, carboxy-methyl cellulose, as well as pectin, guar gum, karaya gum and similar natural gums, starch and derivatives of starch.

When present, such polymer or blend of polymers are typically employed in the hot-melt adhesive matrix at levels that are effective in providing their specific benefits, such as, for example, from about 5% to about 85%, preferably from about 10% to about 75%, and more preferably from about 15% to about 70%, by weight of the composition.

Additional additives for the hot-melt adhesive matrix used in the present invention's compositions may include melt viscosity modifiers, such as plasticizers and waxes.

Examples of suitable plasticizers are paraffinic oils, naphthenic oils, liquid polyisobutylenes, citric acid esters, tartaric acid esters, benzoic acid esters, sucrose esters, stearic acid and isostearic acids and their esters, tri-mellitates, sorbitol, urea, epoxydized vegetal oils, polymerised vegetal oils, castor oil and its derivatives, phthalates, liquid polyesters, liquid polyamides, glycolates, aromatic sulfonamides, C8-C22 organic amides and hydroxy-amides, polyhydric alcohols and their esters, glycerol and its esters like glyceryl benzoates or glyceryl acetates, pentaerythritol and its esters, glycols and polyglycols and their esters and ethers, polyethylene glycol-polypropylene glycol block copolymers, sorbitan esters, liquid phosphate esters, lactic acid and its esters, esters of mono- and dicarboxylic fatty acids (C8-C22) hydrophilically modified by insertion in the molecular chain of 1 to 40 moles of ethylene oxide and/or of propylene oxide per mole of base ester, polyethers and their derivatives, and blends thereof.

Waxes suitable for a hot-melt adhesive matrix apt to be used in the present invention's compositions include, without being limited to, mineral waxes like paraffin and microcrystalline waxes; polyethylene waxes; polyethylene glycol type waxes like those trademarked as the Carbowax brand; oxidized polyethylene waxes; polymethylene waxes, bis-stearamides and other fatty amide waxes; natural and synthetic waxes like beeswax, soywax, carnauba wax, ozokerite, ceresin; waxes derived from both the Fisher-Tropsch and Ziegler-Natta processes; water soluble waxes, polyalkylene waxes.

According to a preferred embodiment of the present invention preferred plasticizers and waxes are polar compounds such as citric acid esters, aromatic sulfonamides, benzoic acid esters, glycols and polyglycols and their ethers and esters, polyhydric alcohols and their esters, glycerol and its esters, sorbitan esters, C8-C22 organic amides and hydroxy-amides, and blends thereof.

When present, such melt viscosity modifier or blend of melt viscosity modifiers are typically employed in the composition at levels that are effective in providing their specific benefits, such as, for example, from about 1% to about 85%, preferably from about 3% to about 75%, and more preferably from about 5% to about 70%, by weight of the composition.

The hot-melt adhesives of the present invention may also comprise tackifiers. Tackifiers suitable for the hot-melt adhesives to be used in the present invention's compositions include, without being limited to, rosins and their derivatives; terpenes and modified terpenes, like terpene-phenolic resins; aliphatic, cycloaliphatic, and aromatic resins like C5 aliphatic resins, C9 aromatic resins, and C5/C9 aliphatic-aromatic resins, hydrogenated hydrocarbon resins, acrylic and aromatic-acrylic resins and their mixtures. In a preferred embodiment of the present invention, the tackifiers are rosins and rosin esters, aromatic and aliphatic-aromatic resins, terpene and terpene-phenolic resins, acrylic and aromatic-acrylic resins, and blends thereof.

When present, such tackifier or blend of tackifiers are typically employed in the composition at levels that are effective in providing their specific benefits, such as, for example, from about zero to about 60% and preferably from about zero to about 40%.

The compositions of the present invention may further include antioxidants, UV adsorbers and stabilizers; inorganic and organic fillers, colored compounds such as pigments and permanent dyes, perfumes biocides and antimicrobial preservatives; antistatic agents; perfumes etc.

Additional Ingredients

Additional ingredients in the wetness indicator compositions of the present invention may comprise, for example, a surfactant or a blend of surfactants.

Surfactants that are suitable for the present invention may include anionic, cationic, nonionic and amphoteric surfactants and any combination thereof; for example, ethoxylated alcohols, fatty alcohols, high molecular weight alcohols, the ethoxylated pareth surfactants like Performathox™ 450 from Baker Hughes Inc., alkoxylated alkylates such as PEG-20 stearate, end group-capped alkoxylated alcohols, alkoxylated glyceryl and polyglyceryl alkylates such as PEG-30 glyceryl stearate, glyceryl alkylates such as glyceryl stearate, alkoxylated hydrogenated castor oil, alkoxylated lanolin and hydrogenated lanolin, sorbitan alkylates and alkoxylated sorbitan alkylates, sugar derived surfactants such as the alkyl glycosides and sugar esters, poloxamers, polysorbates, and sulfo succinic acid alkyl esters, diethyl-hexyl-sodium-sulfosuccinate, sodium dioctyl sulfosuccinates surfactants, 4-1-amino-ethyl-phenol-poly-oxy-ethyl-ene fatty ethers, and poly-oxy-ethylene fatty acid esters.

Other suitable surfactants may be neutral block copolymer surfactants, which can be selected from polyoxypropylene-polyoxyethylene block copolymer, poly [poly(ethylene oxide)-block-poly(propylene oxide)]copolymers or propylene glycol-ethylene glycol block copolymers. Other suitable nonionic surfactants include polyethylene lauryl ether, polyoxyethylene nonyl phenyl ether, polyoxyethylene oleyl phenyl ether, polyethylene glycol monostearate, sorbitan monolaurate, sorbitan trilaurate, polyoxyethylene sorbitan monolaurate, polyoxypropylenesorbitan monolaurate, polyethylene glycol sorbitan monolaurate, polypropylene glycol sorbitan monolaurate, polyalkyne glycol sorbitan monolaurate, sorbitan monopalmitate, sorbitan tripalmitate, polyoxyethylene sorbitan monopalmitate, polyoxypropylenesorbitan monopalmitate, polyethylene glycol sorbitan monopalmitate, polypropylene glycol sorbitan monopalmitate, polyalkyne glycol sorbitan monopalmitate, sorbitan monostearate, sorbitan tristearate, polyoxyethylene sorbitan monostearate, polyoxypropylenesorbitan monostearate, polyethylene glycol sorbitan monostearate, polypropylene glycol sorbitan monostearate, polyalkyne glycol sorbitan monostearate, sorbitan monooleate, sorbitan trioleate, polyoxyethylene sorbitan monooleate, polyoxypropylenesorbitan monooleate, polyethylene glycol sorbitan monooleate, polypropylene glycol sorbitan monooleate, polyalkyne glycol sorbitan monooleate, and similar sorbitan esters and ethoxylated sorbitan esters like the ones marketed by Croda under the Span and Tween trademarks.

It has surprisingly been found that when non-ionic surfactants form more than 5% by weight of the wetness indicator compositions of the present invention, surfactants with not too high HLB values, e.g. lower than 20, are preferable because they help the development of deeper colors from the reaction of the leuco dye(s) with the developer(s), while they also better prevent the premature color formation due e.g. to partial absorption of humidity from air. Therefore when the wetness indicator compositions of the present invention include more than 5% by weight of nonionic surfactant, surfactants with HLB value not higher than 20 are preferable; more preferably the used nonionic surfactants have a HLB value not higher than 16 and most preferably not higher than 10.

When present, such surfactant or blend of surfactants, is typically employed in the wetness indicator compositions of the present invention at levels that are effective in providing their specific benefits, such as, for example, from about 0.001% to about 90% by weight of the composition, preferably from about 0.1% to about 85%, and more preferably from about 1% to about 80%.

EXAMPLES

The present invention is illustrated by the following examples, which are merely for the purpose of illustration and are not to be regarded as limiting the scope of the invention or the manner in which it can be practiced. Unless specifically indicated otherwise, parts and percentages are given by weight.

Example 1

A Wetness Indicator with the Following Composition was Prepared:

| Ingredient | Wt. % on the total weight of the wetness indicator composition | Supplier |
| --- | --- | --- |
| PVP-VA S-630 copolymer | 30.0 | PVP-VA copolymer available from Ashland |
| Span 60 | 42.0 | Non-ionic surfactant available from Croda |
| Carbowax 400 | 24.0 | Polyethylene glycol available from Dow Chemicals |
| Crystal violet lactone (CVL) | 1.0 | Leuco dye available from TCI Chemicals |
| 3,5-di-tert-butyl-salicylic acid (TBSA) | 2.5 | Color developer available from TCI Chemicals |
| Irganox 1010 | 0.5 | Antioxidant stabilizer available from BASF |

The nonionic surfactant Span 60 plus the Irganox 1010 plus half the weight of Carbowax 400 are heated and melted into a stirred stainless steel mixer at a temperature of 110° C. When the mass is completely molten and homogenous, TBSA is suspended into one fourth of the total quantity of Carbowax 400 and added. Then the PVP-VA copolymer is also slowly added to the molten mass, until it is fully incorporated, melted and homogenously mixed. As a final component the CVL, suspended in the remaining Carbowax 400, is added to the molten composition that is further kept under stirring for about 30 minutes for assuring complete homogeneity.

The resulting wetness indicator composition, while still in a molten state, is coated on a polyethylene film, typically used e.g. as a backsheet for hygienic absorbent articles, at a basis weight of about 25 grams/m$^2$.

The coated surface of the wetness indicator composition appears colorless and remains equally colorless even when stored for 24 hours in conditions of high temperature and humidity, e.g. at 40° C. and 75% relative humidity. However if contacted with a drop of liquid water or of human urine the illustrated colorless wetness indicator composition immediately turns to a dark Sapphire blue color in the wet area.

Example 2

The wetness indicator composition of example 1 was prepared in the same way but with the modification that 1% by weight of Span 60 was substituted by 1% by weight of Zinc Oxide added with the rest of Span 60 at the beginning of the preparation. The final wetness indicator composition appears not only distinctly whiter but, when contacted with one drop of water or of human urine, turns immediately to a significantly darker Ultramarine blue color. This behavior shows the beneficial effect on the wet color intensity of the wetness indicator compositions of the present invention, given by the addition in the wetness indicator composition of compounds of polyvalent metals and in particular of Zinc compounds.

Example 3

A Wetness Indicator with the Following Composition was Prepared:

| Ingredient | Wt. % on the total weight of the wetness indicator composition | Supplier |
| --- | --- | --- |
| AC 5120 | 40.0 | Ethylene Acrylic acid copolymer available from Honeywell |
| PVP-VA S-630 copolymer | 13.0 | PVP-VA copolymer available from Ashland |
| Performathox 420 | 24.0 | Non-ionic surfactant available from Baker Hughes |
| Carbowax 400 | 16.0 | Polyethylene glycol available from Dow Chemicals |
| 3-(1,2-Dimethyl-3-indolyl)-3-[4-(diethylamino)-2-methylphenyl]phthalide | 2.0 | Leuco dye available from TCI Chemicals |
| 4-4' di-Hydroxy-benzophenone | 4.5 | Color developer available from TCI Chemicals |
| Irganox 1010 | 0.5 | Antioxidant stabilizer available from BASF |

The wetness indicator composition of Example 3 is prepared in a way similar to Example 1 by initially melting in a stirred stainless steel mixer kept at 120° C., the nonionic surfactant Performathox 420 plus the Irganox 1010 and plus half weight of Carbowax 400. About 15 minutes after the complete melting of the above blend, the developer 4-4' di-Hydroxy-benzophenone is added, after having been suspended into one fourth of the total quantity of Carbowax 400. Then the two polymers AC 5120, first, and PVP-VA, after, are slowly added under continuous stirring until the molten mass is completely homogeneous. Finally the Leuco dye is added together with the remaining Carbowax.

When coated at a basis weight of about 25 grams/m$^2$ on a polyethylene film, the coated wetness indicator composition of Example 3 appears colorless. However when it is contacted with a drop of water or of human urine the wetted area turns quickly to a deep Blue Turquoise.

Example 4

A Wetness Indicator with the Following Composition was Prepared:

| Ingredient | Wt. % on the total weight of the wetness indicator composition | Supplier |
|---|---|---|
| PVP-VA S-630 copolymer | 30.0 | PVP-VA copolymer available from Ashland |
| Span 65 | 38.5 | Non-ionic surfactant available from Croda |
| Carbowax 400 | 20.0 | Polyethylene glycol available from Dow Chemicals |
| Crystal violet lactone (CVL) | 2.0 | Leuco dye available from TCI chemicals |
| Pergafast 201 | 8.5 | Color developer available from BASF |
| Irganox 1010 | 0.5 | Antioxidant stabilizer available from BASF |
| Titanium Dioxide | 0.5 | Pigment available from Huntsman |

The wetness indicator composition of Example 4 is prepared in a way similar to the previous examples. The non-ionic surfactant and half of the Carbowax 400 are melted at 110° C. in a stirred heated stainless steel mixer and mixed with the Irganox 1010 and the Titanium Dioxide. After about 15 minutes of stirring, Pergafast 201 is added after having been suspended in one fourth of the amount of Carbowax 400. After that the molten mass becomes again homogeneous, the PVP-VA copolymer is slowly added under stirring. Finally the CVL leuco dye is added, mixed with the remaining Carbowax 400. Once coated on a polyethylene film at a basis weight of about 25 g/m², the above wetness indicator composition forms a white coating that, when contacted with water or with human urine, turns in a few seconds to a dark Ultramarine blue.

Example 5

A Wetness Indicator with the Following Composition was Prepared:

| Ingredient | Wt. % on the total weight of the wetness indicator composition | Supplier |
|---|---|---|
| Polyox WSR N10 | 22.0 | Polyethylene oxide polymer available from Dow Chemicals |
| Carbowax 8000 | 15.0 | Polyethylene glycol available from Dow Chemicals |
| Carbowax 400 | 50.0 | Polyethylene glycol available from Dow Chemicals |
| Crystal violet lactone (CVL) | 2.0 | Leuco dye available from TCI chemicals |
| Dodecyl Gallate | 10.0 | Color developer available from TCI Chemicals |
| Irganox 1010 | 0.6 | Antioxidant stabilizer available from BASF |
| Tinuvin 770 | 0.2 | UV stabilizer available from BASF |

-continued

| Ingredient | Wt. % on the total weight of the wetness indicator composition | Supplier |
|---|---|---|
| Tinuvin 928 | 0.2 | UV stabilizer available from BASF |

Carbowax 8000, one half of the Carbowax 400, Irganox 1010 and the two Tinuvin stabilizers are heated to 130° C. and melted in a heated stirred stainless steel mixer. When the molten mass is at the desired temperature, the developer Dodecyl Gallate is added together with one fourth of the Carbowax 400. After about 15 minutes of stirring, the Polyox WSR N10 polymer is slowly added until it is homogeneously incorporated into the molten mass. As the final components, the CVL is added together with the rest of the Carbowax 400. The resulting wetness indicator composition is coated on a polyethylene film at a basis weight of about 25 g/m² giving a colorless coating. Said colorless coated wetness indicator composition when contacted with water or with human urine turns immediately, in the wetted areas, to a very dark Ultramarine blue.

Example 6

A Wetness Indicator with the Following Composition was Prepared:

| Ingredient | Wt. % on the totral weight of the wetness indicator composition | Supplier |
|---|---|---|
| PVP-VA S-630 copolymer | 33.0 | PVP-VA copolymer available from Ashland |
| Benzoflex 9-88 | 25.0 | Dipropylene glycol dibenzoate plasticizer available from Eastman |
| Span 20 | 8.5 | Non-ionic surfactant available from Croda |
| Carbowax 4000 | 15.0 | Polyethylene glycol available from Dow Chemicals |
| Carbowax 200 | 10.6 | Polyethylene glycol available from Dow Chemicals |
| Alpha-naphtholphthalein | 0.4 | Leuco dye available from TCI chemicals |
| Sodium stearate | 7.0 | Color developer available from Aldrich |
| Irganox 1010 | 0.5 | Antioxidant stabilizer available from BASF |

Benzoflex 9-88, Carbowax 4000, Span 20 and Irganox 1010 are heated and melted at 110° C. in a heated stirred stainless steel mixer. When the mass is homogeneously melted, Sodium Stearate is suspended in half of the quantity of Carbowax 200 and added to the molten mass. After about 15 minutes of stirring, the PVP-VA copolymer is slowly added and mixed until homogeneously incorporated. Then the leuco dye alpha-naphtholphthalein is added together with the rest of the Carbowax 200. The obtained wetness indicator composition is coated, at a basis weight of about 25 g/m², on a polyethylene film and gives a colorless coating. If some drops of water or of human urine are dripped on the coated wetness indicator composition, the wetted area turns in few seconds to an intense Turquoise blue.

Example 7

A Wetness Indicator with ehe Following Composition was Prepared:

| Ingredient | Wt. % on the total weight of the wetness indicator composition | Supplier |
| --- | --- | --- |
| PVP-VA S-630 copolymer | 30.0 | PVP-VA copolymer available from Ashland |
| Benzoflex 9-88 | 22.0 | Dipropylene glycol dibenzoate plasticizer available from Eastman |
| Span 40 | 12.0 | Non-ionic surfactant available from Croda |
| Carbowax 4000 | 5.0 | Polyethylene glycol available from Dow Chemicals |
| Carbowax 400 | 10.0 | Polyethylene glycol available from Dow Chemicals |
| Diethylene glycol | 14.4 | Plasticizer available from TCI Chemicals |
| Thymolphthalein | 0.1 | Leuco dye available from TCI Chemicals |
| Sodium hydroxide | 3.0 | Color developer available from Aldrich |
| Sodium stearate | 3.0 | Color developer available from Aldrich |
| Irganox 101 | 0.5 | Antioxidant stabilizer available from BASF |

Benzoflex 9-88, Carbowax 4000, Carbowax 400, Span 40 and Irganox 1010 are heated and melted at 110° C. in a heated stirred stainless steel mixer. Separately from the molten mass inside the stirred stainless steel mixer, sodium hydroxide, used as a 50% by weight water solution, is mixed with sodium stearate and half of the quantity of the diethylene glycol. This blend is heated to 90° C. and kept under stirring at this temperature for about thirty minutes, to be sure that all the water introduced with the sodium hydroxide solution has completely evaporated. At this point the blend of sodium hydroxide, sodium stearate and diethylene glycol is mixed into the stirred stainless steel mixer that contains the molten mass at 110° C. When the blend in the stainless steel mixer is homogenously mixed, the copolymer PVP-VA is slowly added until completely melted and dispersed. Then the leuco dye thymolphthalein, blended with the remaining diethylene glycol, is added to the wetness indicator composition. Such wetness indicator composition is coated on a polyethylene film at a basis weight of about 25 g/m², and gives a colorless coating. However when said coating is wetted with water or with human urine, the wet areas turns quickly to a dark Ultramarine blue.

Example 8

A Wetness Indicator with the Following Composition was Prepared:

| Ingredient | Wt. % on the total weight of the wetness indicator composition | Supplier |
| --- | --- | --- |
| PVP-VA S-630 copolymer | 19.0 | PVP-VA copolymer available from Ashland |
| Kraton D 1113 | 15.0 | Styrene-Isoprene-Styrene block copolymer available from Kraton |
| Benzoflex 9-88 | 25.0 | Dipropylene glycol dibenzoate plasticizer available from Eastman |
| Diethylene glycol | 19.8 | Plasticizer available from TCI Chemicals |
| Foral AX | 10.0 | Tackifier available from Eastman |
| Thymolphthalein | 0.2 | Leuco dye available from TCI Chemicals |
| Sodium hydroxide | 3.0 | Color developer available from Aldrich |
| Sodium stearate | 3.0 | Color developer available from Aldrich |
| Span 80 | 3.0 | Non-ionic surfactant available from Croda |
| Irganox 101 | 1.0 | Antioxidant stabilizer available from BASF |
| Titanium Dioxide | 1.0 | Pigment available from Huntsman |

Benzoflex 9-88, Foral AX, Titanium dioxide, Span 80 and Irganox 1010 are heated and melted at 150° C. In such molten mass Kraton D 1113 is slowly added and mixed until completely homogeneous. Then the temperature of the stirred mixer is cooled down, until the molten mass reaches a temperature of 130° C.

Separately from the molten mass, that is kept under stirring inside the mixer, sodium hydroxide, used as a 50% by weight water solution, is mixed with sodium stearate and half of the quantity of the diethylene glycol. This blend is heated to 90° C. and kept under stirring at this temperature for about thirty minutes, to be sure that all the water introduced with the sodium hydroxide solution has completely evaporated. At this point the blend of sodium hydroxide, sodium stearate and diethylene glycol is mixed into the stirred stainless steel mixer that contains the molten mass at 130° C.

Then the PVP-VA copolymer is added under continuous stirring until all the mass is homogeneous. The leuco dye thymolphthalein is finally added, mixed with the remaining diethylene glycol. The obtained molten wetness indicator composition is coated on a polyethylene film at a basis weight of about 25 g/m², giving a white coating. When this white coating is wetted with water or with human urine, the wetted area turns from white to a dark Steel blue in about one minute.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

While particular embodiments of the present invention have been illustrated and described, it would be obvious to those skilled in the art that various other changes and modifications, all within reach of a skilled man in the art, can be made without departing from the spirit and scope of protection of the present invention, which is defined only by the appended claims.

What is claimed is:

1. A wetness indicator hot-melt composition comprising:
   a) from 0.01% to 20% by weight of a leuco dye or of a blend of leuco dyes that changes from colorless to colored in acidic conditions;
   b) from 0.1% to 50% of an organic acidic color developer or of a blend of organic acidic color developers;

c) from 0.1% to 85% by weight of a non-ionic surfactant or of a blend of non-ionic surfactants;

d) from 5% to 60% by weight of a tackifier or of a blend of tackifiers, wherein the leuco dye is crystal violet lactone or the blend of leuco dyes includes crystal violet lactone, the organic acidic color developer or the blend of organic acidic color developers has a solubility in water equal to or lower than 5 grams per liter at 20° C., the non-ionic surfactant or the blend of non-ionic surfactants has an HLB value not higher than 10, and the tackifier or blend of tackifiers is selected from aromatic resins, rosins, rosin esters and blends thereof.

2. The wetness indicator hot-melt composition of claim 1, wherein the organic acidic color developer or the blend of organic acidic color developers is selected from the group comprising gallic acid, propyl gallate, octyl gallate, dodecyl gallate, salicylic acid, acetyl-salicylic acid, sulfo-salicylic acid, 3, 5-di-tert-butylsalicylic acid and its salts and esters, hydroxyl-benzoic acids and their salts and esters, 2 carboxy-phenyl-salicylate, zinc stearate, zinc resinate, and combinations thereof.

3. The wetness indicator hot melt composition of claim 1, further comprising Zinc oxide in an amount not greater than 2% by weight.

4. The wetness indicator hot melt composition of claim 1, further comprising 5% to 85% by weight of said composition of a water-soluble or water dispersible polymer or of a blend of water-soluble or water dispersible polymers.

5. The wetness indicator hot melt composition of claim 4, wherein said water soluble or water dispersible polymer or said blend of water soluble or water dispersible polymers are selected from the group consisting of ethylene-acrylic acid copolymers, polyvinylpyrrolidone, poly-vinyl pyrrolidone-vinyl acetate copolymers, polyamides, sulfopolyesters, poly-vinyl ethers, polyethylene oxides, polyvinyl alcohols, polyacryl-amides, cellulose ethers and esters, hydroxy-propyl-cellulose, salts of polyacrylic acid, starch and derivatives of starch, and combinations thereof.

6. The wetness indicator hot melt composition of claim 1, further comprising from 1% to 85% by weight of said composition of a melt viscosity modifier or of a blend of melt viscosity modifiers.

7. The wetness indicator hot melt composition of claim 6, wherein said melt viscosity modifier or said blend of melt viscosity modifiers is a plasticizer or a wax selected from the group consisting of benzoic acid esters, citric acid esters, tartaric acid esters, sucrose esters, stearic acid esters, isostearic acid esters, trimellitates, sorbitol, epoxydized vegetal oils, liquid polyesters, liquid polyamides, glycolates, aromatic sulfonamides, C8-C22 fatty alcohols, polyhydric alcohols and their esters, glycerol and its esters, pentaerythritol and its esters, glycols and their esters and ethers, and polyglycols and their esters and ethers, polyethylene glycol-polypropylene glycol block copolymers, sorbitan esters, liquid phosphate esters, tricresyl phosphate, and combinations thereof.

8. The wetness indicator hot melt composition of claim 1, wherein said wetness indicator composition changes from one of colorless, white, or translucent appearance to a visible color, or vice versa.

9. An article comprising the wetness indicator hot melt composition of claim 1, wherein said wetness indicator composition is applied on a structural component of the article.

10. A wetness indicator hot-melt composition comprising:
a. from 0.01% to 20% by weight of a leuco dye or of a blend of leuco dyes that changes from colorless to colored in alkaline conditions;
b. from 0.1% to 50% of an organic alkaline color developer or of a blend of organic alkaline color developers;
c. from 0.1% to 85% by weight of a non-ionic surfactant or of a blend of non-ionic surfactants;
d. from 5% to 60% by weight of a tackifier or of a blend of tackifiers wherein the leuco dye or the blend of leuco dyes is selected from thymolphthalein, alpha-naphtholphthalein, 4,5,6, 7-tetrabromo-phenolphthalein, 3',3",5',5" tetrabromo-phenolphthalein, or blends thereof, the organic alkaline color developer or the blend of organic alkaline color developers is selected from the group comprising sodium stearate, potassium stearate, sodium oleate, potassium oleate and combinations thereof, the non-ionic surfactant or the blend of non-ionic surfactants has an HLB value not higher than 10, the tackifier or blend of tackifiers is selected from aromatic resins, rosins, rosin esters and blends thereof.

11. The wetness indicator hot-melt composition indicator composition of claim 10, further comprising from 5% to 85% by weight of said composition of a water soluble or water dispersible polymer or of a blend of water soluble or water dispersible polymers.

12. The wetness indicator hot-melt composition of claim 11, wherein said water soluble or water dispersible polymer or said blend of water soluble or water dispersible polymers are selected from the group consisting of polyvinylpyrrolidone, polyvinylpyrrolidone-vinyl acetate copolymers, ethylene-acrylic acid copolymers, sulfopolyesters, poly-vinyl ethers, polyethylene oxides, polyvinyl alcohols, cellulose ethers, cellulose esters, hydroxy-propyl-cellulose, polyamides, polyacrylamides, salts of polyacrylic acid, starch, derivatives of starch and combinations thereof.

13. The wetness indicator hot-melt composition of claim 10, further comprising from 1% to 85% by weight of said composition of a melt viscosity modifier or of a blend of melt viscosity modifiers.

14. The wetness indicator hot-melt composition as in claim 13, wherein said melt viscosity modifier or said blend of melt viscosity modifiers is a plasticizer or a wax selected from the group consisting of benzoic acid esters, citric acid esters, tartaric acid esters, sucrose esters, stearic acid esters, isostearic acid esters, trimellitates, sorbitol, epoxydized vegetal oils, liquid polyesters, liquid polyamides, glycolates, aromatic sulfonamides, C8-C22 fatty alcohols, polyhydric alcohols and their esters, glycerol, esters of glycerol, pentaerythritol, esters of pentaerythritol, glycols, esters of glycols, ethers of glycols, polyglycols, esters of polyglycols, ethers of polyglycols, polyethylene glycol-polypropylene glycol block copolymers, sorbitan esters, liquid phosphate esters, tricresyl phosphate, and combinations thereof.

15. The wetness indicator hot-melt composition of claim 10, wherein said wetness indicator composition changes from one colorless, white, or translucent appearance to a visible color, or vice versa.

16. An article comprising the wetness indicator hot-melt composition of claim 10, wherein said wetness indicator composition is applied on a structural component of the article.

* * * * *